United States Patent [19]

Fuller

[11] Patent Number: 4,732,147

[45] Date of Patent: Mar. 22, 1988

[54] SUPPORT FRAME

[75] Inventor: David Fuller, Dimchurch, England

[73] Assignee: Smiths Industries Public Limited Company, London, England

[21] Appl. No.: 16,607

[22] Filed: Feb. 19, 1987

[30] Foreign Application Priority Data

Feb. 22, 1986 [GB] United Kingdom ............... 8604433

[51] Int. Cl.⁴ ........................................... A61M 25/02
[52] U.S. Cl. ........................ 128/207.18; 128/207.17; 128/DIG. 26; 604/179
[58] Field of Search ................. 128/207.18, 207.17, 128/DIG. 26; 604/174, 179

[56] References Cited

U.S. PATENT DOCUMENTS

| 853,439 | 5/1907 | Clark | 128/207.18 |
| 2,259,817 | 10/1941 | Hawkins | 128/207.18 |
| 2,590,006 | 3/1952 | Gordon | 128/207.18 |
| 4,018,221 | 4/1977 | Rennie | 128/207.18 |
| 4,120,304 | 10/1978 | Moor | 128/DIG. 26 |
| 4,331,144 | 5/1982 | Wapner | 128/DIG. 26 |

FOREIGN PATENT DOCUMENTS 48112 12/1981 German Democratic Rep. ............... 128/207.18

Primary Examiner—Dalton L. Truluck
Assistant Examiner—F. Wilkens
Attorney, Agent, or Firm—Pollock, Vande Sande and Priddy

[57] ABSTRACT

A plastic support frame for a paediatric naso-tracheal tube comprising a planar pad and an arm which projects from the pad with an adjustable length. The pad has two parallel channels of circular section which extend across the entire width of the pad. Three lateral channels extend between the channels and are located off-center across the width of the pad. The arm has two parallel limbs that are a snap fit in the channels, and a lateral cross piece that is either a snap fit in one of the lateral channels or extends along the rear edge of the pad. The arm has a flange at one end which receives a connector for the tube and has a lug that prevents rotation of the connector.

9 Claims, 8 Drawing Figures

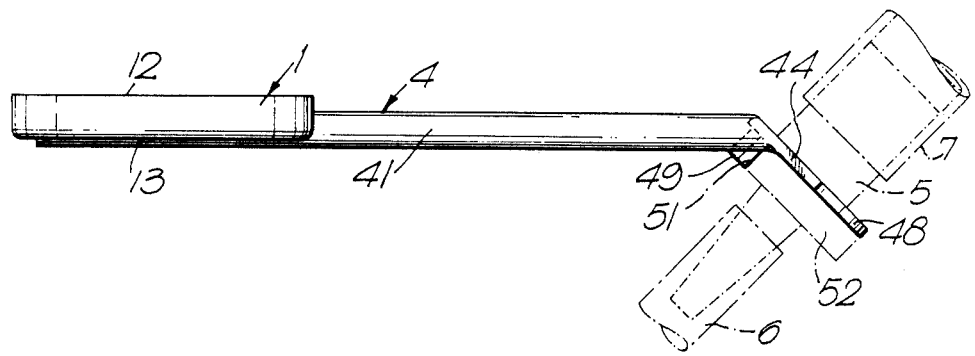
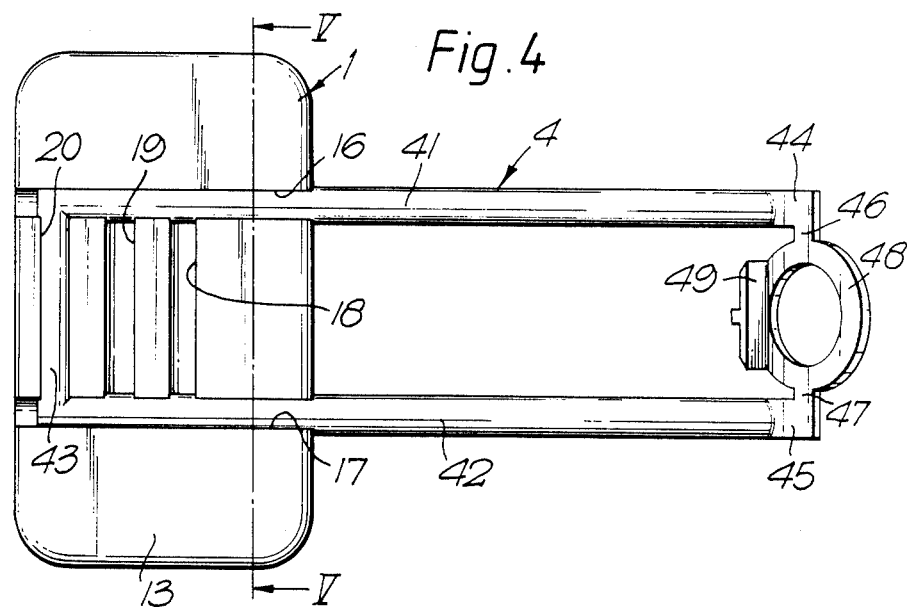
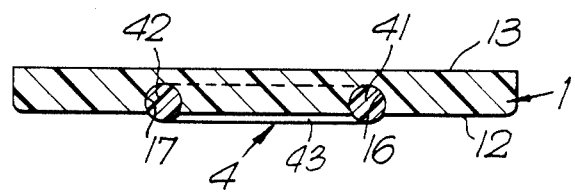

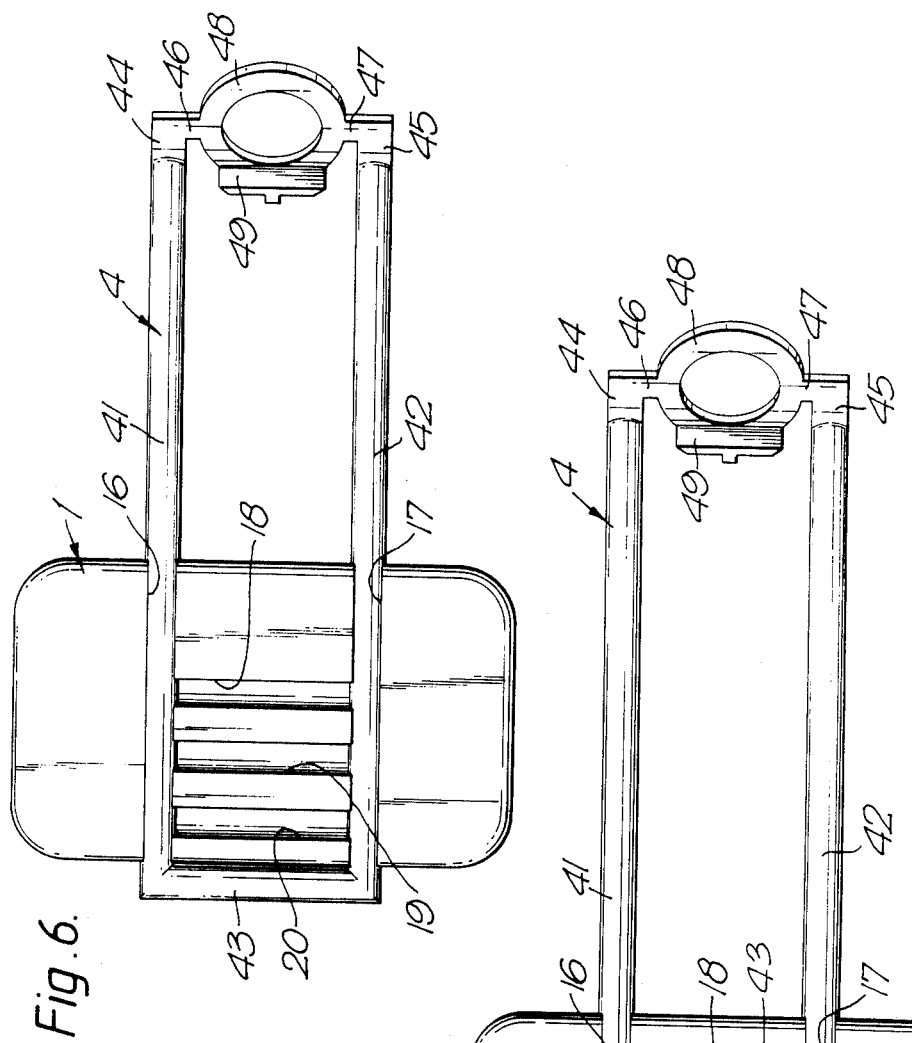

SUPPORT FRAME

BACKGROUND OF THE INVENTION

This invention relates to support frames and more particularly, to frames for supporting medico-surgical tubes for nasal or oral use.

Ventilation and anaesthetic gases can be administered to a patient via a tube that extends into the trachea via the patient's nose or mouth. With young children especially, whose skin is susceptible to damage by relatively light pressure, it is necessary to support the tracheal tube and the weight of connectors and tubing joined with the tracheal tube where it emerges from the patient's nose or mouth. The usual way of providing this support is by a frame of bent wire, such as of the kind described by Reid and Tunstall in Anaesthesia Vol. 21 No. 1, January 1966 pages 72 to 79. This previous frame comprises a generally T-shape loop of metal wire, the base portion of which passes through a metal connector that serves to make connection between the tracheal tube and the oxygen/anaesthetic tubing. The two ends of the wire forming the loop are joined together at the enlarged head portion of the loop which is secured to the forehead of the child such as by a bandage. The frame is suitably bent to ensure that the connector is raised above the child's face and that the weight of the associated tubing is supported.

These previous frames suffer from various disadvantages. Because the frame is integral with a metal connector, the combined weight of the frame and connector is relatively high. The cost of manufacturing a metal frame and connector is relatively large which necessitates re-using and sterilizing the equipment, whereas medical practitioners generally prefer disposable equipment. The area of the frame exerting pressure on the child's forehead is small leading to a localized distribution of pressure and possible discomfort. Furthermore, different size frames have to be used according to the size of the patient, and whether they support a nasal or oral tube. This thereby requires larger stocks to be held by the hospital.

BRIEF SUMMARY OF THE INVENTION

It is an object of the present invention to provide a support frame by which these disadvantages can be alleviated.

According to one aspect of the present invention there is provided a frame for use with a tracheal tube, the frame comprising a generally planar pad member and a support arm member one end of which is adapted to support a connector for mating with the tracheal tube, the other end of the arm being engageable with the pad member, and the length of arm member projecting from the pad member being selectively adjustable.

The arm member is preferably a removable press-fit with the pad member. The arm member may include two parallel limbs extending along the arm member and a lateral cross piece extending between the limbs close to the other end of the arm member. The pad member may have two parallel channels arranged to receive the limbs as a snap fit and at least one lateral channel arranged to receive the lateral cross piece. The lateral channel is preferably located off-center across the width of the pad member. The pad member may include a plurality of lateral channels extending parallel with one another at spaced locations across the width of the pad member. The parallel channels that are arranged to receive the limbs preferably extend across the entire width of the pad member. The limbs and the channels may be of substantially circular cross-section and the same diameter, the channels opening along their length on a surface of the pad member.

Alternatively, the pad member may have a broad channel with a width equal to the width of the arm member. The arm member, in this alternative embodiment, preferably has a planar transverse section at its other end adapted to be received in the broad channel. The planar transverse section is preferably provided with surface formations adapted to engage with co-operating surface formations on the floor of the channel such as thereby to prevent displacement of the arm member along its length in the channel.

The arm member may include a flange at the one end which is adapted to receive the connector. The flange may include a surface formation arranged to engage a co-operating surface formation on the connector such as thereby to prevent rotation of the connector relative to the frame.

The pad member may have surface formations thereon arranged to improve the grip of the pad member with a bandage securing the frame to the patient's head.

The length of the arm member is preferably selectively adjustable to a length in which the one end of the arm member supports a connector of a nasotracheal tube in the region of the nose of a paediatric patient when the pad member is secured to the patient's head. The pad member and the arm member may be of a substantially rigid plastics material. One surface of the pad member may be profiled to the shape of the patient's forehead.

A paediatric naso-tracheal tube support frame in accordance with the present invention, will now be described, by way of example, with reference to the accompanying drawings.

BRIEF DESCRIPTION OF THE DRAWINGS

FIG. 3 is a side elevation view of the frame;

FIG. 4 shows the underside of the frame;

FIG. 5 is a transverse cross-sectional elevation of the frame along the line V—V of FIG. 4;

FIGS. 6 and 7 shows the underside of the frame in different configurations; and

DETAILED DESCRIPTION

Figure 1:
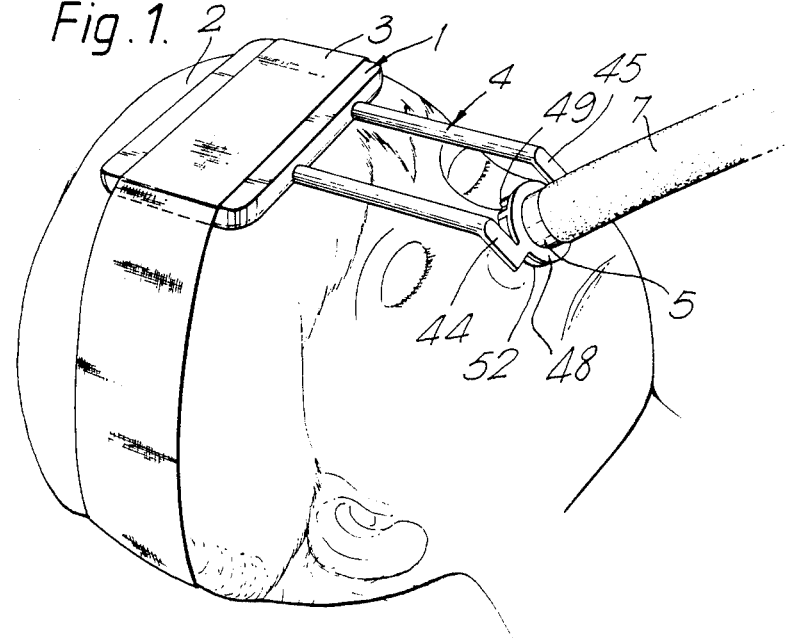
FIG. 1 is a perspective view showing the frame in use on a patient.
Figure 2:
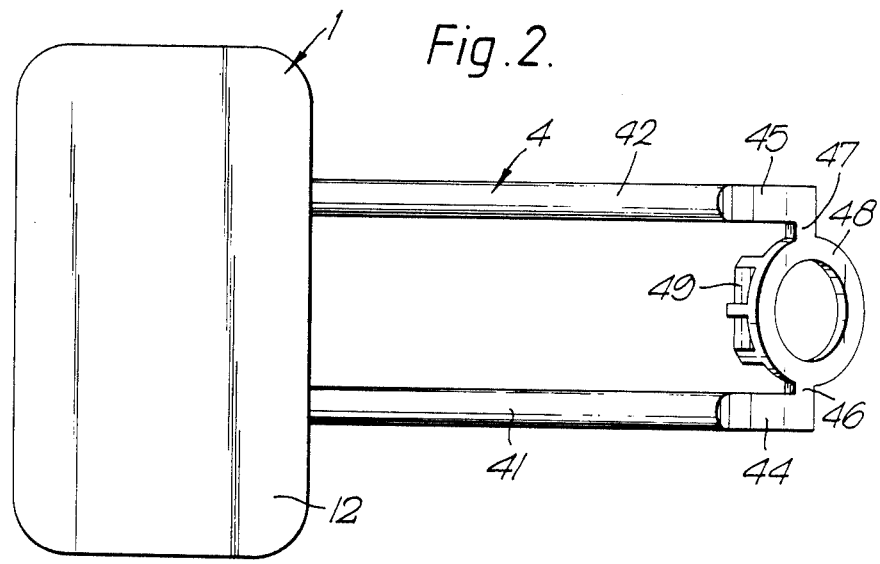
FIG. 2 is a plan view of the upper surface of the frame.

With reference first to FIG. 1, the support frame comprises a pad 1 that is placed on the forehead 2 of the child and is secured thereto by a bandage 3 wrapped around the head. A piece of fabric (not shown) may be placed under the pad 1 to cushion it on the forehead. An arm member 4 projects caudally from one side of the pad 1 above the patient's nose. The arm member 4 supports a plastics paediatric connector 5 that makes connection between the machine end of a naso-tracheal tube and a ventilation line 7, and thereby supports at least some of the weight of the ventilation line.

Referring now also to FIGS. 2 to 5, which show the support frame in greater detail, the pad 1 and arm member 4 are two separate parts of the frame which are both mouldings of a light, relatively rigid plastics material, such as polypropylene. The pad 1 consists of a rectangular planar member 41 mm long by 24 mm wide and 3.5 mm thick. The upper surface 12 of the pad 1 may be ribbed or provided with other surface formations to prevent the pad slipping relative to the bandage 3. The underneath surface 13, that is the surface towards with the patient's skin, may be formed with a relief pattern to improve the grip of the pad. The underneath surface 13 is also provided with channels to receive and secure the arm member 4. Two parallel channels 16 and 17 extend across the entire width of the pad 1, and three channels 18 to 20 extends laterally between the parallel channels at different locations across the width of the pad, opening along their length. As best seen in FIG. 5, the channels 16 to 20 form, in section, the major part of a circle so that the width of the channels where they open on the lower surface 13 of the pad 1 is somewhat less that the maximum width of the channels, internally of the pad.

The arm member 4 comprises two parallel limbs 41 and 42 of circular section and of the same thickness as the width of the channels 16 and 17 so that they are a snap, press-fit in the channels. The limbs 41 and 42 extend along opposite sides of the patient's nose, being spaced from each other by about 14 mm. The limbs 41 and 42 are bridged at their rear end by a lateral crosspiece 43 having the same section as the limbs. The limbs 41 and 42 extend straight to a point 57 mm forwardly of the cross-piece 43, where they are each flattened and inclined downwardly at an angle 0 of 45 degrees to form forward portions 44 and 45. A short lateral finger 46 and 47 extends inwardly from the tip of each forward portion of the limbs, to opposite sides of a circular flange 48 that extends in the plane of the inclined forward portions. The flange 48 has an internal diameter of 8.5 mm and a thickness of about 0.8 mm. A lug 49 projects downwardly from the rear edge of the flange 48 and serves to locate in a flattened edge 51 of a flange 52 of the paediatric connector 5 (FIG. 3). The lug 49 prevents rotation of the connector 5, and hence of the tracheal tube 6 which might otherwise be caused by movement of the attached ventilation line 7.

The length of the arm member 4 to the center of the flange 48 is about 63 mm. The length of arm member 4 that projects from the forward edge of the pad 1, in the configurations shown in FIGS. 2 to 5, where the crosspiece 43 is located in the rear channel 20 is about 40 mm. This length is adjustable by changing the configuration of the frame, that is by changing the position of the arm member 4 relative to the pad 1. This can be achieved by locating the arm member 4 in a more rearward position, as shown in FIG. 6, in which the limbs 41 and 42 extend along the entire length of the channels 16 and 17, and the lateral cross-piece extends along the rear edge of the pad 1. In this configuration, the arm member 4 projects only 34 mm forwardly of the pad 1. The configuration of the frame can also be changed by locating the crosspiece 43 in one of the more forward channels 18 or 19, as shown in FIG. 7. Alternatively, the configuration of the frame can be changed by reorienting the arm member 4 and the pad 1, by rotating the pad through 180 degrees so that the lateral channels 19 and 20 are located closer to that edge of the pad which is now closer the forward end of the arm member.

The support frame described can be made cheaply enough to be disposable. In contrast with previous frames including a connector irremovably mounted on the frame, the frame of the present invention can be used with a range of different size, standard connectors, thereby avoiding the need to stock different frames. Because the frame can be adjusted to suit different size patients, this also avoids the need to stock a range of different size frames. It would also be possible to have frames that could be used for supporting both oral and nasal tubes. The large area contact possible with the planar pad, and the surface finish on both sides of the pad can be chosen to give a firmer, more comfortable location than has been possible with wire frames.

Figure 8:
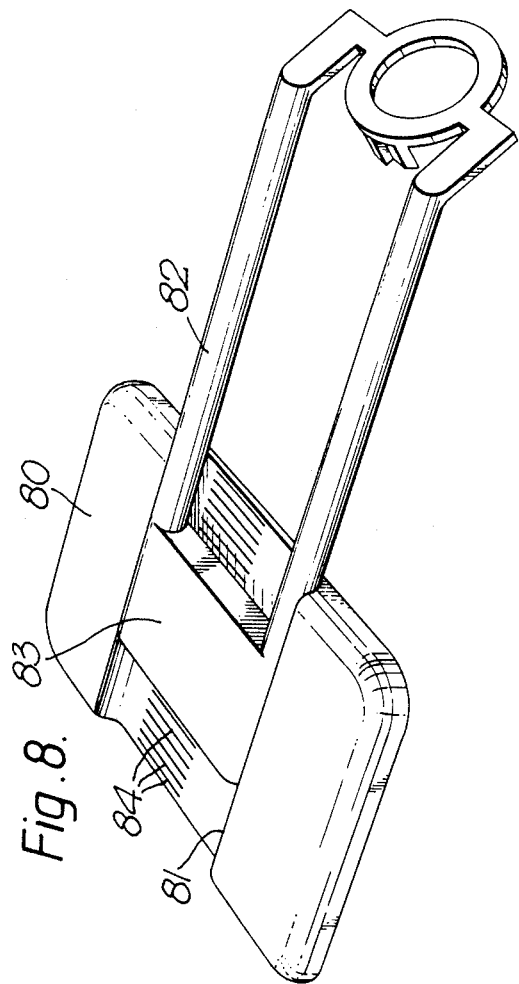
FIG. 8 is a perspective view of an alternative frame.

It will be appreciated that the pad and arm member may take various different shapes and that different arrangements are possible for providing adjustment between the arm member and the pad. For example, as shown in FIG. 8, the pad member 80 may have a broad channel 81 that extends across the entire width of the arm member 82. The arm member 82 has a planar transverse section 83 at its rear end, the underside of which is provided with surface formations (not shown) that engage in surface formations 84 formed on the floor of the channel 81 to prevent the arm member sliding along its length in the channel. In this way, the arm member 82 can be snapped into the channel 81 at any position with the contacting surface formations preventing displacement of the arm member along its length.

The pad can be curved with the same profile as the child's forehead if desired.

What I claim is:

1. A frame for supporting on a patient a tracheal tube having a connector connected therewith, said frame comprising: a generally planar pad member, said pad member having two parallel channels and at least one lateral channel each of which opens on a planar surface of the pad member; and a support arm member, said support arm member having two ends, one of said ends being adapted to support said connector, said support arm member comprising two parallel limbs that extend along the arm member and a lateral cross piece that extends between said limbs close to the other of said ends of the arm member, said two limbs being removably inserted in a press fit into said two parallel channels respectively and said lateral cross piece being inserted into said lateral channel, the length of said arm member projecting from the pad member being selectively adjustable.

2. A frame according to claim 1, wherein said lateral channel is located off-center across the width of the said member pad.

3. A frame according to claim 1, wherein the said pad member includes a plurality of lateral channels extending parallel with one another at spaced locations across the width of the pad member.

4. A frame according to claim 1, wherein the said parallel channels that receive said limbs extend across the entire width of the pad member.

5. A frame according to claim 1, wherein the said limbs and parallel channels are of substantially circular cross-section and the same diameter.

6. A frame according to claim 1, wherein the said arm member has a flange at said one end, said flange being adapted to receive the said connector, the flange having a projection thereon, and the said connector having a projection that engages the projection on the flange such as thereby to prevent rotation of the connector relative to the frame.

7. A frame for supporting on a patient a tracheal tube, said frame comprising: a generally planar pad member adapted for securing to the patient's forehead, said pad member having two parallel channels extending across the entire width of the pad member and a plurality of lateral channels extending between the parallel channels at spaced intervals along the parallel channels, at least one of said lateral channels being located off-center across the width of the pad member; and a support arm member, one end of said support arm member having a flange arranged to support said tracheal tube, said support arm member including two parallel limbs extending along the arm member and located as a press-fit in the said parallel channels to connect said support arm member to said pad member, and a lateral cross piece extending between the said limbs at the other end of the arm member, said lateral cross piece being located in a selected one of said lateral channels or outside said pad member such of said lateral channels or outside said pad member such that the length of the said arm member projecting from the pad member is selectively adjustable.

8. A frame for supporting on a patient a tracheal tube having a connector connected therewith, said frame comprising: a generally planar pad member, said pad member having a broad channel therein that opens on a planar surface of the pad member; and a support arm member, said support arm member having two ends, one of said ends being adapted to support said connector, said support arm member comprising two parallel limbs and a lateral cross piece extending between the limbs close to the other of said ends of the arm member, the width of the said arm member being defined by said two parallel limbs and said lateral cross piece extending therebetween, said width of said arm member being equal to the width of the said channel, the arm member being located in the channel as a removable press fit to removably connect said arm member to said pad member, and the length of said arm member projecting from said pad member being selectively adjustable.

9. A frame according to claim 8, wherein the said arm member has a generally planar transverse section at its said other end that is located in the said broad channel, the floor of the channel being provided with surface projections, and the said planar transverse section being provided with surface projections that engage with the said surface projections on the channel such as thereby to prevent displacement of said arm member along its length in the channel.

* * * * *